United States Patent
Fukuyama et al.

(10) Patent No.: US 7,728,867 B2
(45) Date of Patent: Jun. 1, 2010

(54) ELECTRONIC ENDOSCOPE SYSTEM

(75) Inventors: Mitsufumi Fukuyama, Hyogo (JP); Go Matsui, Saitama (JP)

(73) Assignee: Hoya Corporation, Tokyo (JP)

( * ) Notice: Subject to any disclaimer, the term of this patent is extended or adjusted under 35 U.S.C. 154(b) by 875 days.

(21) Appl. No.: 11/466,904

(22) Filed: Aug. 24, 2006

(65) Prior Publication Data
US 2007/0046798 A1 Mar. 1, 2007

(30) Foreign Application Priority Data
Aug. 25, 2005 (JP) .................... P2005-243793

(51) Int. Cl.
*H04N 9/68* (2006.01)
*H04N 5/262* (2006.01)
(52) U.S. Cl. ........................ 348/65; 348/239
(58) Field of Classification Search .............. 348/65, 348/70, 96, 239
See application file for complete search history.

(56) References Cited

U.S. PATENT DOCUMENTS 5,142,359 A * 8/1992 Yamamori ............... 348/70
5,479,204 A * 12/1995 Iwamatsu ............... 348/96
6,201,571 B1 * 3/2001 Ota .......................... 348/239
6,421,078 B1 * 7/2002 Akai et al. ............... 348/65
6,879,339 B2   4/2005 Ozawa

FOREIGN PATENT DOCUMENTS

JP    11-197103    7/1999

OTHER PUBLICATIONS

English language Abstract of JP 11-197103.

* cited by examiner

*Primary Examiner*—Gims S Philippe
(74) *Attorney, Agent, or Firm*—Greenblum & Bernstein P.L.C.

(57) ABSTRACT

An electronic endoscope system comprises a video-scope, an imaging device, and a black balance processor. The imaging device, which is provided on the video-scope, is exposed at a normal shutter speed so as to generate an image signal corresponding to an optical image that is formed thereon. The black balance processor generates a black balance value for adjusting the black balance of the image signal, based on a black image signal corresponding to a black image. The black image signal is generated by exposing the imaging device at a high shutter speed that is faster than the normal shutter speed.

19 Claims, 4 Drawing Sheets

ELECTRONIC ENDOSCOPE SYSTEM

BACKGROUND OF THE INVENTION

1. Field of the Invention

The present invention relates to an electronic endoscope system that adjusts a black balance of an image signal.

2. Description of the Related Art

An endoscope system is composed of a video-processor, and a video-scope and a monitor that are connected to the video-processor. The video-scope is provided with an imaging device (for example, a CCD) on a tip portion thereof. The imaging device generates image signals corresponding to an optical image that is formed at the tip portion, and the image signals are output on the monitor as the moving image, after image processing at the video-processor.

The endoscope can be attached to or removed from the video-processor easily, and several types of the video-scope can be attached to the video-processor. The characteristic of the imaging device is different according to the type of the video-scope; therefore, the black balance of the image signals that are input to the video-processor is different according to which type of the video-scope is attached thereto.

Conventionally, the black balance adjustment is conducted in the video-processor using a black balance value in order to maintain an appropriate black balance of the image signals. Because the characteristics of the image device are different according to the type of the video-scope, the black balance value needs to be recomputed whenever the type of the attached video-scope is changed.

However, the tip portion of the video-scope needs to be blacked out by a shading instrument when the black balance value is calculated. Therefore, it leaves the complicated work to the user when the type of the attached video-scope is changed.

In order to eliminate the complicated work, the black balance values regarding the several types of video-scope are stored in the memory in the video-processor, and the black balance value is read from the memory according to the type of the attached video-scope, as shown in Japanese Unexamined Patent Publication (KOKAI) NO. 11-197103. In this system, the black balance value is automatically set up according to the type of the attached video-scope.

However, the black balance of the image signal may be different according to the temperature in the operation room where the video-scope is used, or the degree of deterioration of the light source for illuminating an object, even if the same type of video-scope is attached to the same video-processor. Therefore, the black balance cannot be correctly adjusted if the black balance value is set only based on the type of the video-scope.

Recently, the auto fluorescent endoscope system has been put to practical use. In this system, a lesion, such as one of cancer, in an organ is identified by the auto-fluorescence, which the tissue emits when excitation light is illuminated thereto. The auto-fluorescence which the tissue emits is very weak; therefore, the image signal based on the auto-fluorescence needs to be amplified before it is displayed on the monitor. Due to amplification, the auto-fluorescent image that is displayed on the monitor is greatly influenced by a small change in black balance. Accordingly, it is necessary more precisely to adjust the black balance of the auto-fluorescent image than the black balance of a normal image.

SUMMARY OF THE INVENTION

Therefore, an object of the present invention is to provide an electronic endoscope system that is capable of adjusting the black balance of the image signal precisely and easily.

According to the present invention, there is provided an electronic endoscope system that comprises a video-scope, an imaging device, and a black balance processor. The imaging device, which is provided on the video-scope, is exposed at a normal shutter speed so as to generate an image signal corresponding to an optical image that is formed thereon. The black balance processor generates a black balance value for adjusting the black balance of the image signal based on a black image signal corresponding to a black image. The black image signal is generated by exposing the imaging device at a high speed shutter speed that is faster than the normal shutter speed.

The system preferably comprises an illumination apparatus that illuminates a light from the video-scope onto an object. The imaging device is exposed at the normal shutter speed so as to generate the image signal while the light is being illuminated. The optical image is formed from the light reflected off the object. The image signal device is exposed at the high shutter speed so as to generate the black image signal while the light is not being illuminated.

The black balance processor generates the black balance value based on the black image signal corresponding to a partial area of the black image, for example. In this case, the black balance processor generates the black balance value based on the partial area having the lowest luminance value in a plurality of partial areas in the black image, preferably.

The black image can be based on one field or on one frame of the black image signal. Further, the black image can be based on one frame of the black image signals that is an average of no fewer than two frames of the black image signal.

The high-speed shutter speed is preferably not more than $1/1000$ second long. The system further preferably comprises a black adjustment processor, which adjusts the black balance of the image signal based on the black balance value.

BRIEF DESCRIPTION OF THE DRAWINGS

The objects and advantages of the present invention will be better understood from the following description, with reference to the accompanying drawings in which:

FIG. 2 is a flowchart of the routine in which the power is turned on;

DESCRIPTION OF THE PREFERRED EMBODIMENTS

Figure 1:
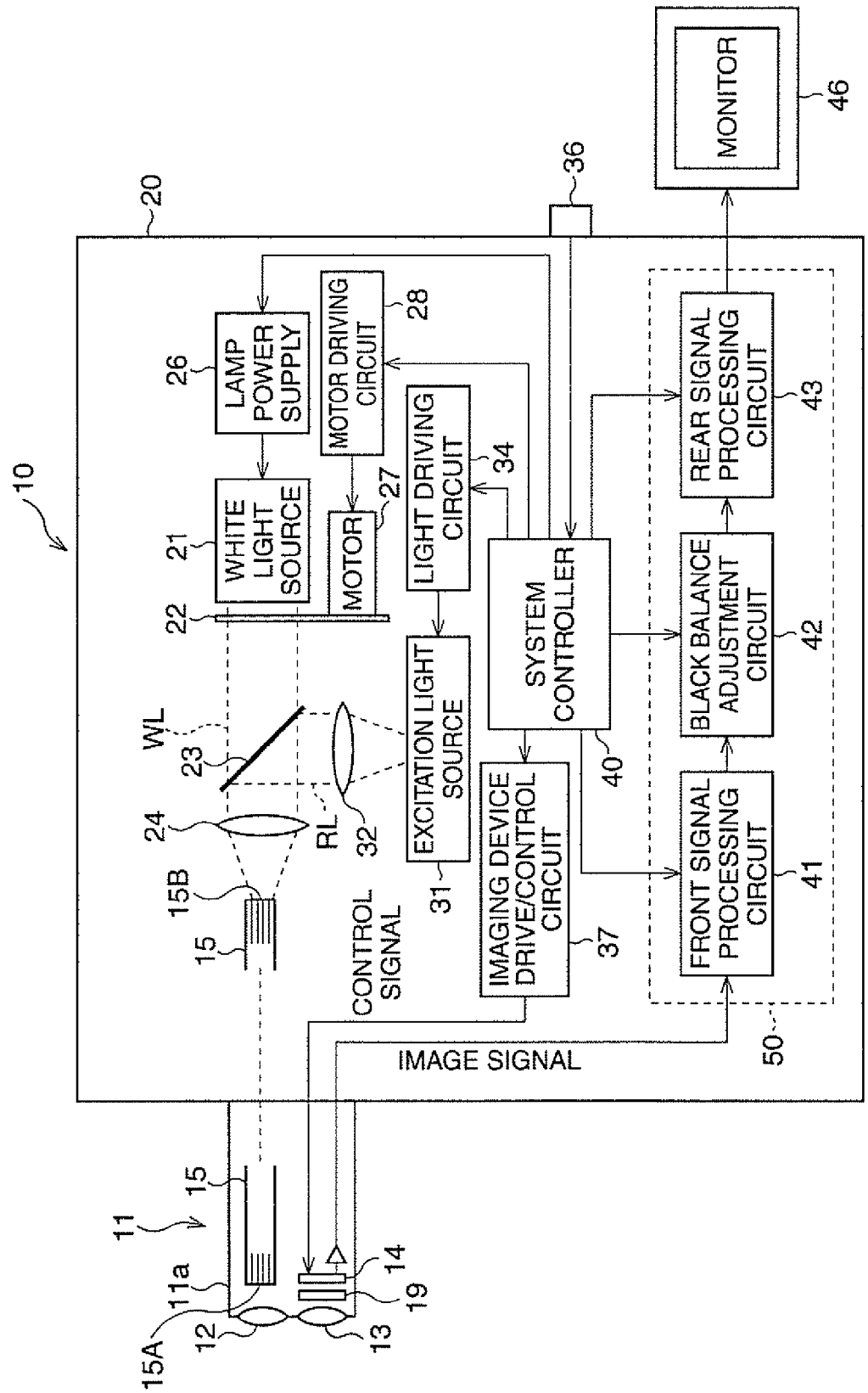
FIG. 1 is block diagram of an electronic endoscope system.

The present invention will be described below with reference to the embodiments shown in the drawings.

FIG. 1 is a block diagram of an electronic endoscope system. The electronic endoscope system 10 has a video-processor 20, a video-scope 11, and a monitor 46, which are connected to the video-processor 20.

The video-scope 11, which is inserted into a body for observing a tissue in an organ, can be attached to or removed from the video-processor 20. The video-scope 11 has a diffusion lens 12, an objective lens 13, a light guide 15, an excitation light cut filter 19, and an imaging device 14. The diffusion lens 12 and the objective lens 13 are disposed on a tip portion 11a of the video-scope 11. The excitation light cut filter 19 and the imaging device 14 are disposed in this sequence on the back of the objective lens 13 on the optical axis of the objective lens 13. The light guide 15 is inserted into the video-scope 11. An output end 15A of the light guide 15 is disposed on the back of the diffusion lens 12 on the optical axis of the diffusion lens 12, and an incident end 15B of the light guide 15 is disposed in the video-processor 20.

The video-processor 20 has a system controller 40 that controls a lamp power supply 26, a motor driving circuit 28, a light driving circuit 34, an imaging device drive/control circuit 37, and an image processing block 50 in the video-processor 20.

The video-processor 20 has a white light source 21 (for example, a xenon lamp) that emits the white light WL, and an excitation light source 31 (for example, a laser light source) that emits the excitation light RL. The lamp power supply 26 applies the voltage to the white light source 21, so that the white light source 21 emits the white light WL. The excitation light source 31 is driven by the light driving circuit 34.

The white light WL passes from right to left in FIG. 1 through a diaphragm 22 and a dichroic mirror 23 so as to be incident to the condensing lens 24. The excitation light RL, which emits from the excitation light source 31 from down to up in FIG. 1 as the diffusing light, is collimated to a parallel excitation light RL by a collimate lens 32. The parallel excitation light RL, which is reflected by the dichroic mirror 23, passes from right to left in FIG. 1 similarly to the white light WL, so as to be incident to the condensing lens 24. The white or excitation light WL or RL, which is condensed by the condensing lens 24, is incident to the light guide 15 at the incident end 15B. The white light WL or the excitation light RL, which passes through the light guide 15, is illuminated onto the tissue (an object) in the organ from the output end 15 (namely, from the tip portion 11a).

Whether the white light WL is illuminated onto the object is controlled by the voltage applied to the white light source 21. The quantity of white light WL that is illuminated onto the object is controlled by the diaphragm 22, which is adjusted by a motor 27. The motor 27 is driven by the motor driving circuit 28. Whether the excitation light RL is illuminated onto the object and the quantity of the excitation light that is illuminated onto the object is adjusted by the light driving circuit 34.

In the electronic endoscope system 10, whether a normal image or an auto-fluorescent image is generated is determined according to the user's indication. When a mode switch 36 that is provided on the video-processor 20 is turned on, the auto-fluorescent image is generated. When the mode switch 36 is turned off, the normal image is generated.

In the state where a power of the processor 20 is turned on when the mode switch 36 is turned off, the white light WL is illuminated onto the object, but the excitation light RL is not. On the other hand, in the state where the power of the processor 20 is turned on when the mode switch 36 is turned on, the excitation light RL is illuminated onto the object, but the white light WL is not.

The white light WL, which is illuminated from the tip portion 11a, is reflected off the object. The reflected white light is received at a photo-sensor area of the imaging device 14 via the objective lens 13 so as to form a normal optical image based on the reflected white light. On the other hand, when the excitation light RL is illuminated from the tip portion 11a onto the object, the object enters into an excited state and emits auto-fluorescence. The auto-fluorescence is received at the photo-sensor area via the objective lens 13 so as to form a fluorescent optical image based on the auto-fluorescence. Further, the excitation light RL that is reflected off the object is absorbed by the excitation light cut filter 19, so the excitation light RL is not incident to the imaging device 14.

The photo-sensor area of the imaging device 14 is composed of a plurality of horizontal lines that are arranged in a vertical direction. Each horizontal line has a plurality of pixels, which are arranged on the horizontal line. While the imaging device 14 is being exposed at a normal shutter speed (the normal shutter speed is for the moving image, for example), each pixel on the imaging device 14 is storing an electrical charge corresponding to the normal optical image or the fluorescent optical image, for an exposure period corresponding to the normal shutter speed. The stored electrical charge in each pixel is transformed to a pixel image signal. Further, the normal shutter speed is in a range between $\frac{1}{200}$ and $\frac{1}{50}$ second, for example. The pixel image signals that are generated at two pixels adjoining each other in the vertical direction are mixed and are read out. In this way, all the pixel signals are read out, so that one field of image signals is read out and is input to the image processing block 50. After the one field of the image signals is read out, next another field of image signals is generated and read out similarly. Due to this, one frame of image signals is read out and is input to the image processing block 50. The storage of the electrical charge at the image device 14, the reading-out of image signals, and the exposure period are all controlled by control signals. The control signals are output from the imaging device drive/control circuit 37 to the imaging device 14. The storage of the electrical charge at the imaging device 14 and the reading-out image signals are successively repeated. Further, the imaging device 14 has the function of an electronic shutter, therefore, the shutter speed is that of an electronic shutter.

When the white light WL is illuminated from the tip portion 11a, the imaging device 14 generates normal image signals corresponding to the normal optical image that is formed at the imaging device 14 based on the white reflected light off the object. On the other hand, when the excitation light RL is illuminated from the tip portion 11a, the imaging device 14 generates fluorescent image signals corresponding to the fluorescent optical image that is formed at the imaging device 14 based on the auto-fluorescence emitted by the object.

The image processing block 50 includes a front signal processing circuit 41, a black balance adjustment circuit 42, and a rear signal processing circuit 43. At the image processing block 50, the image signals are processed according to a predetermined image processing process, as described below.

When the image signals that are input to the image processing block 50 are the normal image signals (namely, when the mode switch 36 is turned off), the normal image signals that are analog image signals undergo several necessary image processes, including contrast adjustment, and are converted to digital image signals at the front signal processing circuit 41. At the black balance adjustment circuit 42, the black balance of the digital image signals is adjusted using a black balance value that is generated in advance (how to generate this value is described below). The digital image signals of which the black balance has been adjusted undergo several necessary image processes, including color adjustment, and are converted to analog image signals at the rear signal processing circuit 43. The analog image signals are output to the monitor 46 as one field of the normal image. The analog image signals repeatedly are generated and are output to the monitor 46 successively, so that the normal image is displayed on the monitor 46 as the moving image.

When the image signals that are input to the image processing block 50 are the fluorescent image signals (namely, when the mode switch 36 is turned on), the image signals undergo image processing for the fluorescent image at the image processing block 50. Namely, the fluorescent image signals (analog image signals) undergo several necessary image processes, including contrast adjustment, and are converted to digital image signals at the front signal processing circuit 41, similarly to with the normal image. After that, at the black balance adjustment circuit 42, the black balance of the fluorescent image signals is adjusted using the black balance value, similarly to with the normal image. Next, a gain of each color signal RGB of the fluorescent image signals is amplified at the rear signal processing circuit 43. After amplifying gain, the fluorescent image signals undergo the same image processing as the normal image signals, and are converted to analog image signals at the rear signal processing circuit 43. The analog image signals are repeatedly output to the monitor 46 successively, so that the fluorescent image is displayed on the monitor 46 as the moving image.

The method of generation of the black balance value will be explained below. When the imaging device 14 is exposed at a high shutter speed (for example, 1/10000 second), which is much faster than the normal shutter speed, the imaging device 14 hardly receives the light without blacking out the tip portion 11a by the shading instrument. Namely, the image that is generated at the imaging device 14 can be a black image when the imaging device 14 is exposed at the high shutter speed. Accordingly, the black balance value for adjusting the black balance value is obtained based on the color signals RGB of the image signals that are generated by exposing the imaging device 14 at the high shutter speed, in this embodiment.

Figure 2:
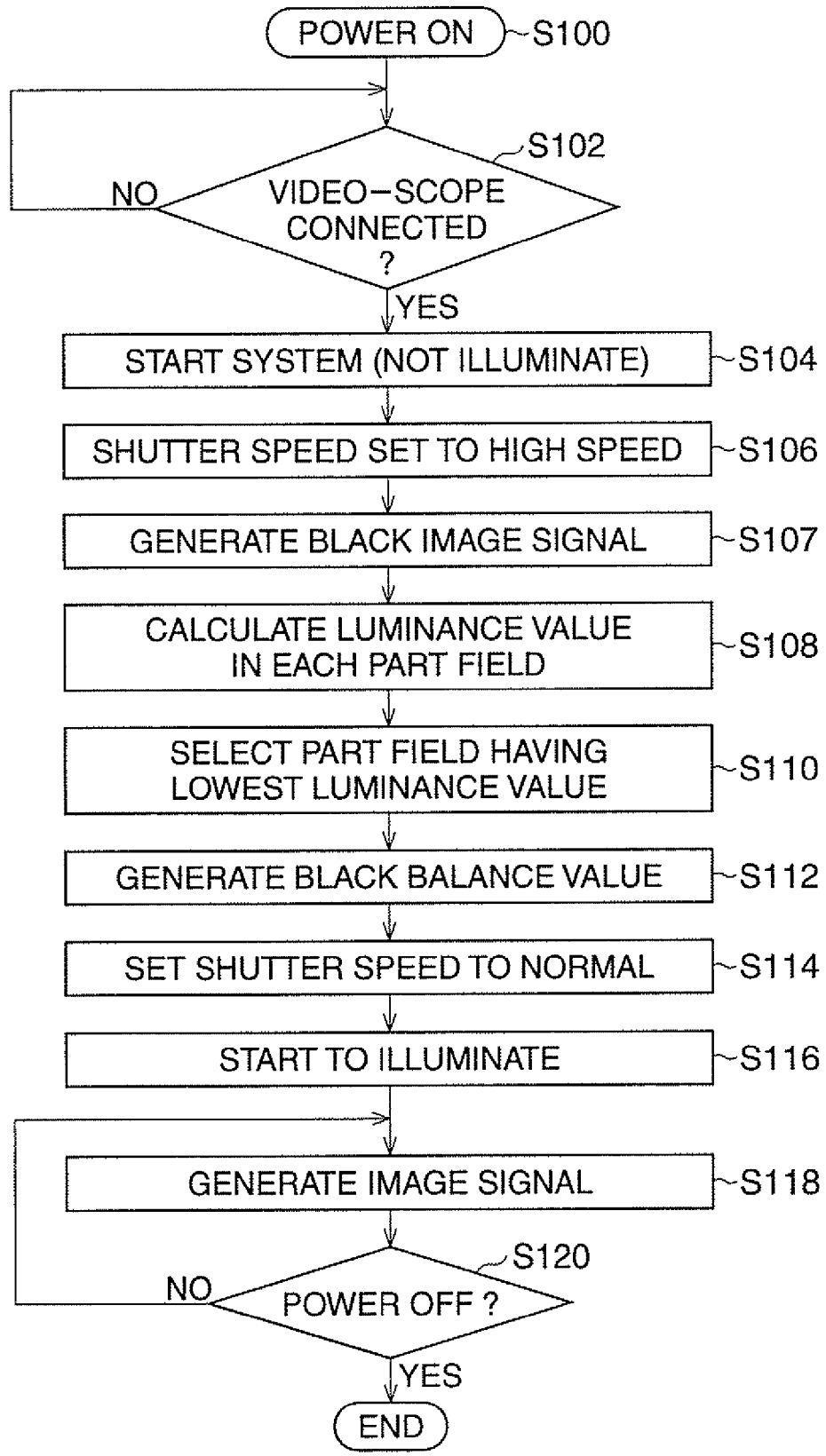
Figure 3:
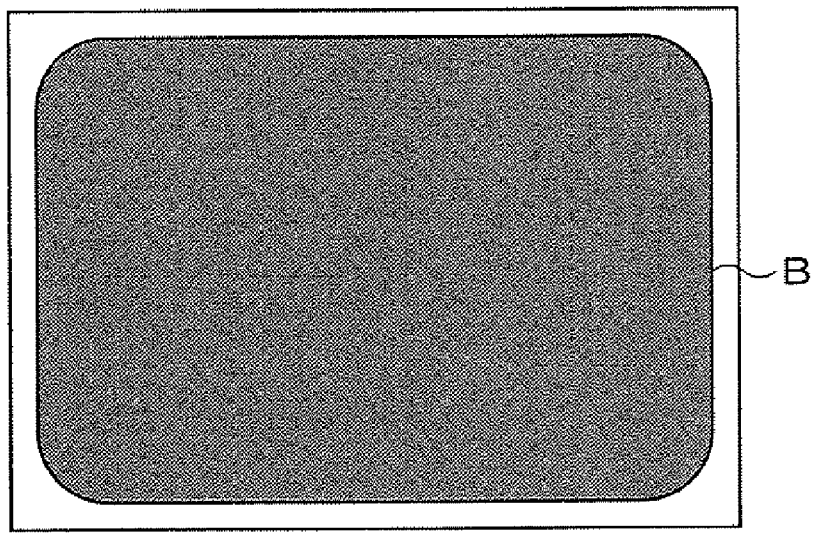
FIG. 3 is a schematic view of the black image.
Figure 4:
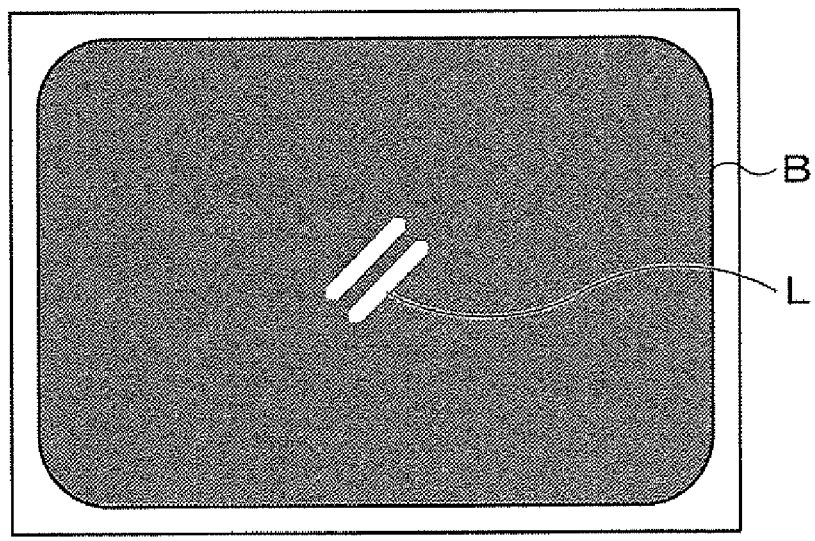
FIG. 4 is a schematic view of the black image when a bright part appears thereon.
Figure 5:
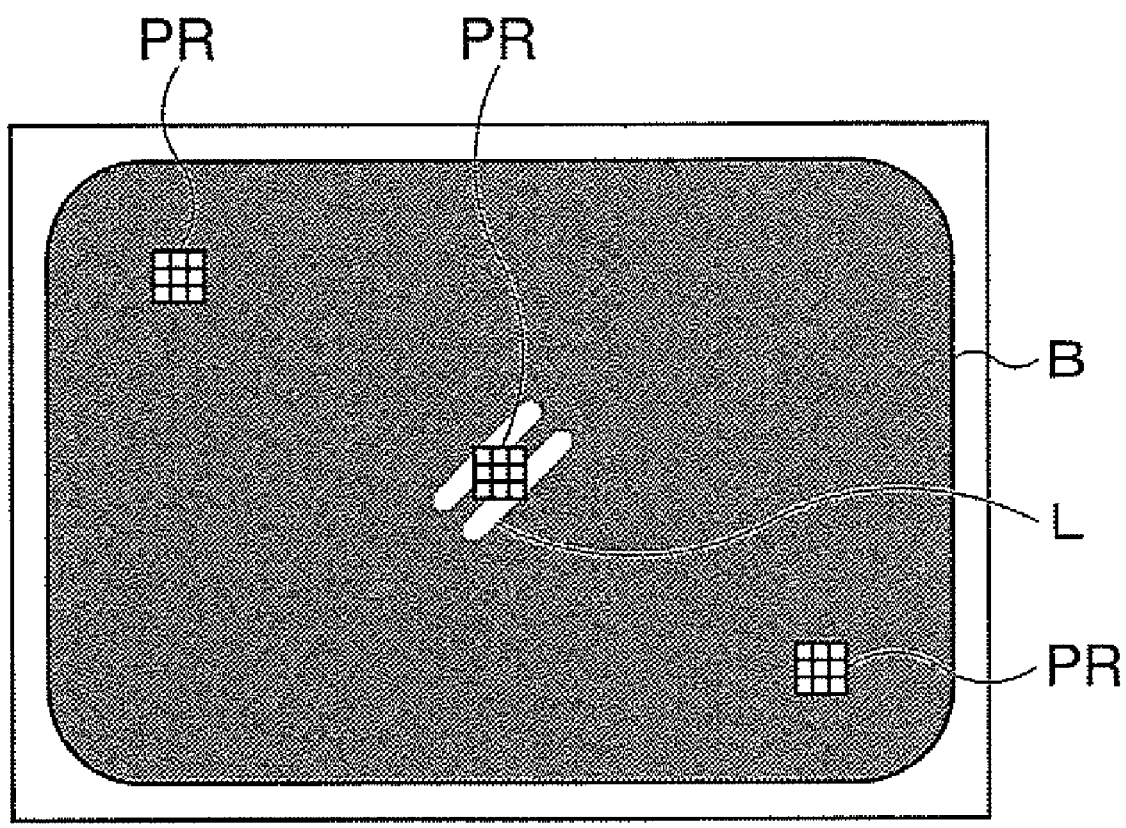
FIG. 5 is a schematic view of the black image for indicating a partial area.

Next, the method of generation of the black balance value will be explained in detail using FIGS. 2-5. FIG. 2 is a flowchart of the routine in which the power of the processor 20 is turned on. FIGS. 3-5 are schematic views of the black image that is generated when the power is turned on.

As shown in FIG. 2, after the power of the processor 20 turns on at step S100, whether the video-scope 11 is attached to the video-processor 20 is determined at step S102. If it is determined that the video-scope 11 is not attached, this routine waits at step S102. If it is determined that the video-scope 11 is attached, the actual work of the electronic endoscope system 10 starts at step S104. Further, the white light WL and the excitation light RL are not illuminated onto the object at step S104.

At step S106, the shutter speed for the imaging device 14 is set to the high shutter speed. At step S107, one frame of the black image signals corresponding to the black image B as shown in FIG. 3 is generated, as described below.

Namely, at step S107, the imaging device 14 is being exposed for the exposure period corresponding to the high shutter speed, so that the electrical charges are stored and are transferred to the image signals (the black image signals). Due to this, one field of the black image signals is generated as the analog signals. The one field of the black image signals is read out from the imaging device 14, and is input to the front signal processing circuit 41. At the front signal processing circuit 41, one field of the black image signals, which undergoes the predetermined image processing, is converted to the digital signals, and is input to the black balance circuit 42.

Next another field of the black image signals is generated by exposing the imaging device 14 at the high shutter speed and is read out from the imaging device 14, after the previous field of the black image signals has been read out. Due to this, one frame of black image signals is obtained.

The exposure of the imaging device 14 at the high shutter speed is repeated, so that a plurality of frames (for example, 8 frames) of the black image signals are generated and are input to the black balance adjustment circuit 42 through the front signal processing circuit 41. At the black balance adjustment circuit 42, the average of a plurality of frames of the black image signals are calculated and is generated as the one frame of the black image signals. Further, the one frame of the black image signals is input to the monitor 46 through the rear signal processing circuit 43.

An image corresponding to the one frame of the black image signals that is generated at step S107 is shown in FIGS. 3 and 4. One frame of the black image signals is generated by exposing the imaging device 14 at the high shutter speed, when both the white light WL and the excitation light RL are not being emitted. Therefore, the image corresponding to the one frame of the black image signals is usually a black image B on which nothing appears, as shown in FIG. 3.

However, the tip portion 11a is usually placed out of the body immediately after the power of the processor 20 is turned on. Therefore, the tip portion 11a is placed under a different light source from the light sources 21 and 31; namely, it is placed under an indoor light source (for example, an indoor fluorescent lamp) of the operation room. If the light illuminated by the indoor light source is directly incident to the imaging device 14, a part of the photo-sensor area of the imaging device 14 receives the directly incident light, so that a bright part L may appear on the part of the black image B because of the directly incident light, as shown in FIG. 4.

The black image signals in the bright part L should not be referred to as the black balance value. Accordingly, a plurality of (for example, three) partial areas PR are designated in the black image B as shown in FIG. 5, and the black balance value is generated from the black image signals in one of the a plurality of the partial areas which does not include the bright part L at steps S108-S112.

At step S108, a luminance value of the black image signals in each partial area PR is calculated. Further, the luminance value is the arithmetical mean of luminance values in each partial area PR. At step S110, the luminance value in every partial area PR is compared with every other, and the partial area PR having the lowest luminance value is selected. Next, at step S112, the black balance value for adjusting black balance is generated based on the black image signals in the selected partial area PR. In this embodiment, the arithmetical mean of the color signals (R, G, B) in the selected partial area PR becomes the black balance value. For example, if the arithmetical mean of the color signals (R, G, B) in the selected partial area PR is (1, 2, 0), then (1, 2, 0) becomes the black balance value.

After generating the black balance value, the shutter speed for the imaging device 14 is set to the normal shutter speed, from the high shutter speed at step 114. Next, the white light WL or the excitation light RL begins to be illuminated onto the object from the tip portion 11a, according to the input at the mode switch 36 (Step 116).

At step S118, the object is photographed at the imaging device 14; namely, the image signals (normal image signals or fluorescent image signals) are generated at the imaging device 14 at the normal shutter speed. Further, when the white light WL is emitted, the normal image signals are generated, and when the excitation light RL is emitted, the fluorescent image signals are generated at the imaging device 14. The image signals are processed according to the predetermined image processes, as described above, in the circuits 41, 42, and 43. Furthermore, in the black balance adjustment circuit 42, the black balance of the image signals is adjusted, as described below, using the black balance value that is generated at step S112. Namely, the black level of one of the color signals RGB in the image signals is set to the standard black level, and the black levels of other two of the color signals RGB are adjusted to coincide with the standard black level. For example, when the black balance value is (1, 2, 0) and the black level of the color signal R is set to the standard black level, each value of the color signal R is not adjusted; on the other hand, "1" is subtracted from each value of the color signal G and "1" is added to each value of the color signal B. After image processing, the image signals are input to the monitor 46, and are displayed as the moving image (normal image or fluorescent image).

At step S120, whether the power is turned off is determined. If the power is turned off, this routine finishes. If the power is not turned off, step S118 is repeated.

In this embodiment, the black balance value for adjusting the black balance is obtained without using the shading instrument, so that the black balance value can be obtained without a complicated operation. In addition, the shutter speed for the imaging device 14 is adjusted to high speed in order to prevent the imaging device 14 from receiving the light when the imaging device 14 generates the black image signals. Due to this, the black balance value is correctly generated based on the black signals, so that the correct image can be displayed on the monitor 46 without disruption in the black balance even if the image signals are amplified in the case of the fluorescent image signals. Furthermore, the black image for generating the black balance value is obtained when the white light WL and the excitation light RL are not emitted; therefore, the black balance value is correctly generated.

As described above, the high shutter speed for obtaining the black balance value is adjusted to 1/10000 second in this embodiment. However, if the black image can be obtained, the high shutter speed can be adjusted to another setting, for example, to not more than 1/1000 second. Normally, the high shutter speed is adjusted to not more than 1/10000 second for obtaining the correct black balance value.

In this embodiment, the black balance value is generated based on a plurality of frames of the black image signals, but can also be generated based on something other than a plurality of frames of the black image signals. For example, the black balance value can be generated based on one frame, one field, one line, or one pixel of the black image signals in the black image B.

In this embodiment, one each of the normal image and the fluorescent image is displayed on the monitor 46 according to the input at the switch 36. However, both the normal image and the fluorescent image are simultaneously displayed on the monitor 46. In this case, the white light WL and the excitation light RL are illuminated onto the object from the tip portion 11a alternately in each field, so that the normal image signals and the fluorescent image signals are generated alternately in each field. The normal image signals and the fluorescent image signals are synthesized into one frame image signal corresponding to the image that is composed of the normal image and the fluorescent image arranged right to left.

Further, the routine, as shown in FIG. 2, is automatically performed when the power is turned on in this embodiment, but the routine can also be automatically performed when the video-scope 11 is inserted into the body.

In this embodiment, when the black image signals are obtained, the illumination of the white light WL from the tip portion 11a is stopped by controlling the voltage to the lamp power supply 26. However, the illumination of the white light WL can be stopped by blocking out the passage of the white light WL by the diaphragm 22.

Furthermore, the number of the designated partial areas PR for obtaining the black balance value is three in this embodiment, but is not limited to three; namely, no fewer than two partial areas PR can be designated. Further, the partial areas PR are arranged on a diagonal line of the black image B in this embodiment, but the position where the partial areas PR are arranged is not limited to the diagonal line. For example, the partial areas PR can be arranged at random in the black image B. Further, if the number of the partial areas PR is nine, each partial area PR is arranged at the center of each of nine divided areas which the black area B is divided into in a 3×3 matrix.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2005-243793 (filed on Aug. 25, 2005), which is expressly incorporated herein, by reference, in its entirety.

The invention claimed is:

1. An electronic endoscope system, comprising:
   a video-scope;
   an imaging device that is provided on said video-scope, and that is exposed at a normal shutter speed so as to generate an image signal corresponding to an optical image that is formed on the imaging device
   an illumination apparatus that illuminates a light from said video-scope onto an object, wherein said imaging device is exposed at said normal shutter speed so as to generate said image signal while said light is illuminated by said illumination apparatus, and said optical image is formed from said light reflected from the object, and
   a black balance processor that generates a black balance value for adjusting the black balance of said image signal based on a black image signal corresponding to a black image, said black image signal being generated by exposing said imaging device at a high shutter speed that is faster than said normal shutter speed,
   wherein said imaging device is exposed at said high shutter speed so as to generate said black image signal while said light is not illuminated by said illuminating apparatus.

2. An electronic endoscope system according to claim 1, wherein said black balance processor generates said black balance value based on said black image signal corresponding to a partial area of said black image.

3. An electronic endoscope system according to claim 2, wherein said black balance processor generates said black balance value based on said partial area having the lowest luminance value in a plurality of partial areas in said black image.

4. An electronic endo scope system according to claim 1, wherein said black image is based on one field or one frame of said black image signal.

5. An electronic endoscope system according to claim 1, wherein said black image is based on one frame of said black image signals which is an average of no fewer than two frames of said black image signal.

6. An electronic endoscope system according to claim 1, wherein said high speed shutter is not more than 1/1000 second.

7. An electronic endoscope system according to claim 1, further comprising a black adjustment processor that adjusts the black balance of said image signal based on said black balance value.

8. An electronic endoscope system, comprising:
a video-scope;
an imaging device that is provided on said video-scope, and that is exposed at a normal shutter speed so as to generate an image signal corresponding to an optical image that is formed on the imaging device; and
a black balance processor that generates a black balance value for adjusting the black balance of said image signal based on a black image signal corresponding to a black image, said black image signal being generated by exposing said imaging device at a high shutter speed that is faster than said normal shutter speed,
wherein said black balance processor generates said black balance value based on said black image signal corresponding to a partial area of said black image, and
wherein said black balance processor generates said black balance value based on said partial area having the lowest luminance value of a plurality of partial areas in said black image.

9. The electronic endoscope system according to claim 1, said black balance processor generates said black balance value based upon a partial area of the black image having a lowest calculated luminance value of a plurality of partial areas of the black image.

10. The electronic endo scope system according to claim 1, wherein the luminance value in each of the plurality of partial areas of the black image is calculated as the arithmetic mean of color signals in the partial area.

11. The electronic endoscope system according to claim 1, further comprising a controller that, after said black balance value is generated, sets the normal shutter speed and controls the illumination apparatus to emit light.

12. The electronic endoscope system according to claim 1, said black balance processor being configured to generate the black balance value upon supply of power to the electronic endoscope system.

13. The electronic endoscope system according to claim 1, wherein the high shutter speed is determined such that the black image is obtained even when light is not blocked from being incident onto the imaging device.

14. The electronic endoscope system according to claim 8, wherein the high shutter speed is determined such that the black image is obtained even when light is not blocked from being incident onto the imaging device.

15. The electronic endoscope system according to claim 1, wherein said black balance processor calculates the black balance value.

16. The electronic endo scope system according to claim 8, wherein said black image is based on one field or one frame of said black image signal.

17. The electronic endoscope system according to claim 8, wherein said black image is based on one frame of said black image signals which is an average of no fewer than two frames of said black image signal.

18. The electronic endo scope system according to claim 8, wherein said high speed shutter speed is not more than 1/1000 second.

19. The electronic endoscope system according to claim 8, further comprising a black adjustment processor that adjusts the black balance of said image signal based on said black balance value.

* * * * *